United States Patent [19]

Köenig et al.

[11] 4,160,080

[45] Jul. 3, 1979

[54] PROCESS FOR THE PREPARATION OF ALLOPHANATES WHICH CONTAIN ISOCYANATE GROUPS

[75] Inventors: Kalus Köenig, Leverkusen; Wolfgang Reichmann, Dusseldorf; Josef Pedain, Cologne, all of Fed. Rep. of Germany

[73] Assignee: Bayer Aktiengesellschaft, Leverkusen, Fed. Rep. of Germany

[21] Appl. No.: 920,562

[22] Filed: Jun. 29, 1978

[30] Foreign Application Priority Data

Jul. 2, 1977 [DE] Fed. Rep. of Germany ....... 2729990

[51] Int. Cl.$^2$ .................... C08G 18/79; C07C 118/00
[52] U.S. Cl. ................................. 528/59; 260/453 P; 260/453 AL; 528/67
[58] Field of Search ............... 528/59, 67; 260/453 P, 260/453 AL

[56] References Cited

U.S. PATENT DOCUMENTS 3,734,941 5/1973 Sydor ............................. 260/453 P
3,883,571 5/1975 Allport et al. ...................... 528/59

FOREIGN PATENT DOCUMENTS 994890 6/1965 United Kingdom.

OTHER PUBLICATIONS

D.O.S. 2,009,179, Bayer A/G, Sep. 16, 1971.
D.O.S. 2,040,645, Bayer A/G, Mar. 9, 1972.
Kogon, Journ. Am. Chem. Soc., vol. 78, 1956, pp. 4911–4914.

Primary Examiner—H. S. Cockeram
Attorney, Agent, or Firm—Gene Harsh; Lawrence S. Pope

[57] ABSTRACT

The present invention relates to a process for the preparation of allophanates containing aliphatically and/or cycloaliphatically bound isocyanate groups by the reaction of organic compounds containing urethane groups with organic polyisocyanates containing aliphatically and/or cycloaliphatically bound isocyanate groups, characterized in that the reaction is carried out in the presence of strong acids which form a mixed carbamic acid anhydride with aliphatic or cycloaliphatic isocyanates. The present invention also relates to the allophanates produced therefrom.

13 Claims, No Drawings

PROCESS FOR THE PREPARATION OF ALLOPHANATES WHICH CONTAIN ISOCYANATE GROUPS

BACKGROUND OF THE DISCLOSURE

In British Pat. No. 994,890, a process is described for the preparation of organic polyisocyanates in which urethane isocyanates represented by the general formula

$$R'(O-CO-NH-R-NCO)_n$$

in which
R' represents a monovalent or polyvalent organic group of a mono-functional or poly-functional hydroxyl compound,
n represents an integer of from 1 to 6 and
R represents a bi-functional organic group
are reacted with excess diisocyanates either by heat alone or in the presence of metal carboxylates, metal chelates or tertiary amines as catalysts until the fall in the isocyanate content corresponds to complete reaction of the urethane groups present with the isocyanate groups. The exact constitution of the reaction products cannot be specified exactly according to the teaching of the said British Patent. From the isocyanate values measured in the reaction mixtures and the end products isolated from them, it is concluded that the reaction products consist substantially of allophanate polyisocyanates. On closer analytical study of the products obtained according to this process by IR-Spectroscopy and, particularly, by gel chromatographic investigation, it is found that a considerable proportion consists of isocyanurate polyisocyanates and uretdione polyisocyanates formed by the dimerization and trimerization of isocyanate groups which take place as side reactions. If the reaction is stopped when the isocyanate content reached the value calculated for complete allophanatization, one urethane group is left unreacted in the reaction mixture for every isocyanate group which has been used up in a side reaction.

The occurrence of trimerization and dimerization as side reactions in the reactions according to the teaching of British Pat. No. 994,890 is not surprising since, in the absence of catalysts, long reaction times at relatively high temperatures are required until the isocyanate content falls to the value calculated for a complete reaction of the urethane groups (e.g. 24 hours at 130° to 135° C. in Example 1, page 3, lines 49 to 51), and the formation of isocyanurates from allophanates and isocyanates or dimers of these isocyanates is well known in the literature as described by J. C. Kogon, Journ. Am. Chem. Soc., Vol. 78, 1956, pages 4911 to 4914.

Although the use of catalysts makes it possible for much lower reaction temperatures to be employed (compare page 2, lines 92–95 of the British reference), it has long been known that the catalysts described (metal carboxylates, metal chelates, tertiary amines) are excellent dimerization and trimerization catalysts for isocyanates, so that one might expect such side reactions to occur to a considerable extent in the reaction of urethane groups with isocyanates to form allophanates.

The side reactions to form dimers and trimers of polyisocyanates, which cannot be excluded in the process according to British Pat. No. 994,890, lead to reaction mixtures which differ from the corresponding pure allophanate polyisocyanates mainly by being less compatible with many polyhydroxyl compound, particularly with polyhydroxypolyacrylates of the kind used as reactants for polyisocyanates in the production of polyurethane resins.

The problem of preparing pure allophanate polyisocyanates, i.e. allophanate polyisocyanates which are not "contaminated" with dimeric and, particularly, with trimeric polyisocyanates, has already been referred to in German Auslegeschrifts Nos. 2,009,179 and 2,040,645. The processes described therein, however, are aimed at producing allophanate polyisocyanates which contain aromatically bound isocyanate groups. According to the teaching of these prior publications, such compounds can be obtained free from the above mentioned side products if the addition reaction leading to the allophanate polyisocyanate is carried out in the presence of alkylating substances as described in German Auslegeschrift No. 2,009,179 and optionally in the presence of certain metal compounds as catalysts as described in German Auslegeschrift No. 2,040,645. The processes according to German Auslegeschrift Nos. 2,009,179 and 2,040,645 are not however, suitable for the preparation of allophanate polyisocyanates having aliphatically and/or cycloaliphatically bound isocyanate groups. This is clear, for example, from the fact that the isocyanate content of a reaction mixture of a urethane and an aliphatic polyisocyanate falls to only an insignificant extent over a period of 50 hours at 160° to 170° C. When metal catalysts according to German Auslegeschrift No. 2,040,645 were used in such a reaction, only a 66% reaction was observed over a period of 35 hours at 110° to 120° C., and the reaction mixture was by that time severely discolored. In the known state of the art, therefore, there is no process available for the production of pure, light colored allophanate polyisocyanates having aliphatically or cycloaliphatically bound isocyanate groups.

It was an object of the present invention to provide such a process.

It was surprisingly found that this problem could be solved by carrying out the reaction between aliphatic or cycloaliphatic polyisocyanates and compounds containing urethane groups in the presence of certain acids which will be described in more detail below.

BRIEF SUMMARY OF THE INVENTION

The present invention relates to a process for the preparation of allophanates containing aliphatically and/or cycloaliphatically bound isocyanate groups by the reaction of organic compounds containing urethane groups with organic polyisocyanates containing aliphatically and/or cycloaliphatically bound isocyanate groups, characterized in that the reaction is carried out in the presence of strong acids which form a mixed carbamic acid anhydride with aliphatic or cycloaliphatic isocyanates. The present invention also relates to the allophanates which contain aliphatically and/or cycloaliphatically bound isocyanate groups produced by said process.

DETAILED DESCRIPTION OF THE INVENTION

Any organic compounds which contain urethane groups and, optionally, aliphatically or cycloaliphatically bound isocyanate groups and are otherwise inert under the reaction conditions may be used as starting materials for the process according to the invention. These compounds are generally obtained by the reaction of isocyanates with compounds which contain alcoholic or phenolic hydroxyl groups, but the process according to the invention may also be carried out with urethanes obtained, for example, by the reaction of chloroformic acid esters with amines which contain primary amino groups or by any other method. According to a particular embodiment of the process of the invention, urethanes prepared in situ from phenols or alcohols and excess quantities of aliphatic or cycloaliphatic polyisocyanates are used as starting materials. The mixture obtained from this reaction already contains the second main component of the process according to the invention, the aliphatic or cycloaliphatic polyisocyanate which was used in excess for the preparation of the urethane. Among the preferred compounds with urethane groups used as starting materials for the process according to the invention are those represented by the general formula

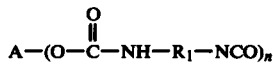

in which

A represents a group of the kind obtained by removal of the hydroxyl groups from an organic compound with a valency of n which contains hydroxyl groups and which, apart from its hydroxyl groups, is inert towards isocyanate groups;

$R_1$ represents a group of the kind obtained by removal of the isocyanate groups from a diisocyanate which has aliphatically and/or cycloaliphatically bound isocyanate groups, and n represents an integer of from 1 to 4.

According to these processes, the preferred urethanes with isocyanate groups used for the process according to the invention, which are represented by the above general formula, are preferably prepared by reacting hydroxyl compounds of the formula

with diisocyanates of the formula

using at least n mols of the diisocyanate per mol of the hydroxyl compound. This reaction which leads to the urethane-containing compounds used as starting materials for the process according to the invention may also be carried out using less than n mols of a diisocyanate per mol of hydroxyl-containing compound $A(OH)_n$, i.e. the quantity of diisocyanate is calculated to lie within the range of from about 0.5 n to 1 n mol per mol of hydroxyl-containing compound. In this case, starting materials containing more than n urethane groups would be formed, because of the chain lengthening reaction which would take place via the urethane groups. Urethane-containing compounds $A(OH)_n$ with monoisocyanates and/or higher than di-functional polyisocyanates, optionally as mixtures with diisocyanates, and which may have no free isocyanate groups, could also be used.

The preparation of the starting materials containing urethane groups for the process according to the invention is carried out by the methods well known in polyurethane chemistry, i.e. by simply heating the starting materials to temperatures of from about 40° to 150° C. preferably from about 50° to 100° C.

The polyhydroxyl compounds $A(OH)_n$ may be either phenols such as phenol, δ-naphthol, cresol, resorcinol or tris-hydroxybenzenes or organic compounds which contain alcoholic hydroxyl groups. Such compounds containing alcoholic hydroxyl groups are preferred to the phenols mentioned above as examples.

These preferred compounds which contain alcoholic hydroxyl groups $A(OH)_n$ include the following:

1. Low molecular weight monohydric to tetrahydric aliphatic alcohols having a molecular weight in the range of from about 32 to 250 which may contain ether bridges, e.g. methanol; ethanol; propanol; isopropanol; isomeric butanols; allyl alcohol; pentanols, hexanols and heptanols; 2-ethylhexanol; fatty alcohols having 10 to 20 carbon atoms; ethanediol; propanediol-(1,2) and -(1,3); butanediol-(1,2); -(1,3) and -(1,4); pentanediol-(1,5); neopentylglycol; hexanediol-(1,6) and -(2,5); 3-methylpentanediol-(1,5); 2-methyl-2-propyl-propanediol-(1,3); 2,2-diethyl-propanediol-(1,3); 2-ethylhexanediol-(1,3); 2,2,4-trimethylpentanediol-(1,3); trimethylhexanediol-(1,6); decanediol-(1,10); dodecanediol-(1,12); 2-butanediol-(1,4); 2-methylene-propanediol-(1,3); glycerol; butanetriol; 2-hydroxymethyl-2-methylpropanediol-(1,3); 1,2,6-hexanetriol; trimethylolethane; trimethylolpropane; pentaerythritol; ethyleneglycol monoalkyl- or monoaryl-ether; propyleneglycol monoalkyl ether; diethyleneglycol; triethyleneglycol; tetraethyleneglycol.

2. Cycloaliphatic monovalent to tetravalent alcohols with molecular weights of from about 88 to 250, e.g. cyclopentanol; cyclohexanol; methylcyclohexanol; trimethylcyclohexanol; 4-tertiarybutyl-cyclohexanol, menthol; borneol and isoborneol; 2-hydroxydecaline; 1,2-; 1,3- and 1,4-cyclohexanediol; 2,4-dihydroxy-1,1,3,3-tetramethylcyclobutane; 1,4-bis-hydroxymethyl-cyclohexane; bis-(4-hydroxycyclohexyl)-methane; 2,2-bis-(4-hydroxycyclohexyl)-propane; 2-methyl-2,4-bis-(4-hydroxycyclohexyl)-pentane; furfuryl- and tetrahydrofurfuryl-alcohol; bis-hydroxymethyl-norbornane; dihydroxymethyl-tricyclodecane.

3. Araliphatic monohydric to tetrahydric alcohols with molecular weights from about 103 to 300, e.g. benzyl alcohol; phenylethyl alcohol; 3-phenylpropanol and 4,4'-di-(2-hydroxyethyl)-diphenylmethane or 4. Polythioethers, polyacetals, polycarbonates or particularly polyesters or polyethers, all containing from about one to four hydroxyl groups, of the kind known in polyurethane chemistry, with average molecular weights of from about 250 to 5,000, preferably from about 300 to 2,000. Suitable polyesters with hydroxyl groups include, for example, the reaction products of polyhydric, preferably dihydric alcohols to which trihydric alcohols may be added with polybasic, preferably dibasic carboxylic acids. Instead of free polycarboxylic acids, the corresponding polycarboxylic acid anhydrides or the corresponding polycarboxylic acid esters of lower alcohols or mixtures thereof may be used for preparing the polyesters. The polycarboxylic acids may be aliphatic, cycloaliphatic, aromatic and/or heterocyclic and they may be substituted, e.g. by halogen atoms, and/or unsaturated. The following are mentioned as examples.

Succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids such as oleic acid which may be mixed with monomeric fatty acids, dimethyl terephthalate and terephthalic acid-bis-glycol esters. The following are examples of suitable polyhydric alcohols:

Ethylene glycol, propylene glycol-(1,2) and -(1,3), butylene glycol-(1,4) and -(2,3), hexanediol-(1,6), octanediol-(1,8), neopentylglycol, cyclohexanedimethanol (1,4-bis-hydroxymethylcyclohexane), 2-methyl-1,3-propanediol, glycerol, trimethylolpropane, hexanetriol-(1,2,6), butanediol-(1,2,4), trimethylolethane, pentaerythritol, quinitol, mannitol and sorbitol, methylglycoside, diethylene glycol, triethylene glycol, tetraethylene glycol, polyethylene glycols, dipropylene glycol, polypropylene glycols, dibutylene glycol and polybutylene glycols. Polyesters of lactones such as ε-caprolactone or hydroxycarboxylic acids such as ω-hydroxycaproic acid may also be used.

The polyethers used according to the invention which have from one to four hydroxyl groups are also known per se and are prepared, for example, by the polymerization of epoxides such as ethylene oxide, propylene oxide, butylene oxide, tetrahydrofuran, styrene oxide or epichlorohydrin, either each on its own, e.g. in the presence of borontrifluoride, or by addition of these epoxides, either as mixtures or successively, to starting components having reactive hydrogen atoms, such as alcohols or phenols, e.g. water ethylene glycol, propylene glycol-(1,3) or -(1,2), trimethylolpropane or 4,4'-dihydroxyl-diphenylpropane.

Particularly to be mentioned among the polythioethers are the condensation products obtained by reacting thiodiglycol on its own and/or with other glycols, dicarboxylic acids or formaldehyde. The products obtained are polythio mixed ethers, polythio ether esters or polythio ether polyacetals, depending on the cocomponents.

Suitable polyacetals include, for example, the compounds which can be prepared from glycols such as diethylene glycol, triethylene glycol, 4,4'-dioxethoxydiphenyl dimethylmethane, hexanediol and formaldehyde. Suitable polyacetals for the purpose of the invention may also be prepared by the polymerization of cyclic acetals.

The polycarbonates with hydroxyl groups used may be of the kind known per se, for example those which can be prepared by the reaction of diols such as propanediol-(1,3), butanediol-(1,4) and/or hexanediol-(1,6), diethylene glycol, triethylene glycol or tetraethylene glycol with diarylcarbonates, e.g. with diphenylcarbonate or phosgene.

The simple aliphatic alcohols mentioned under 1 and the polyester polyols and polyether polyols mentioned under 4 are preferred for the process according to the invention.

Mixtures of the hydroxyl compounds mentioned above may, of course, be used. This is in fact a preferred embodiment of the process according to the invention since, by using a mixture of hydroxyl compounds differing in their functionality, the functionality of the allophanate-polyisocyanate obtained may be adjusted as desired.

According to the invention, the isocyanates used both for preparing the urethane-containing compounds required as starting materials for the process according to the invention and as reactants for these urethane-containing compounds are preferably diisocyanates of the formula $$R_2(NCO)_2$$

in which $R_2$ represents an aliphatic hydrocarbon group with from about 2 to 20, preferably from about 6 to 10 carbon atoms, a cycloaliphatic hydrocarbon group with from about 4 to 20, preferably from about 6 to 15 carbon atoms or a xylylene group.

The following are examples of such isocyanates: ethylene diisocyanate; tetramethylene diisocyanate; hexamethylene diisocyanate; undecamethylene diisocyanate; 2,4,4-trimethyl-1,6-diisocyanatohexane; 3-isocyanatomethyl-3,5,5-trimethyl-cyclohexylisocyanate; 1,3-diisocyanatocyclobutane; 1,4-diisocyanatocyclohexane; 4,4'-diisocyanato-dicyclohexylmethane; 1,2-bis-(isocyanatomethyl)cyclobutane; trimethylhexane-1,6-diisocyanate; 1,11-diisocyanato-undecane; 3-isocyanatomethyl-3,5,5-trimethylcyclohexyl isocyanate; 4,4'-cyclohexane diisocyanate; 4,4'-dicyclohexylmethane-diisocyanate; 1,2-bis-(isocyanatomethyl)-cyclobutane, bis-isocyanatomethyl-norbornane (isomeric mixture); 3(4), 8(9)-diisocyanatomethyl-tricyclo-(5,2,1,0$^{2,6}$)-decane and p-xylylene diisocyanate. Diisocyanates of this kind are used both for preparing the urethane-containing compounds used for the process according to the invention and as the compounds to be reacted with them. Hexamethylene diisocyanate is the preferred diisocyanate for both steps.

For preparing the urethane-containing compounds used as starting materials but not as their reactants for the process according to the invention, monoisocyanates such as n-hexylisocyanate or cyclohexylisocyanate may also be used as part or all of the isocyanate components, although this is less preferred.

Higher than difunctional aliphatic and cycloaliphatic polyisocyanates may also be used as part or all of the isocyanate component both for preparing the urethane-containing compounds used as starting materials and as reactants for these starting materials. Examples of such polyisocyanates include the trimerization products of hexamethylenediisocyanate or of 3-isocyanatomethyl-3,5,5-trimethyl-cyclohexylisocyanate which contain isocyanurate groups.

Any mixture of the above mentioned isocyanates may be used, both for preparing the urethane-containing starting materials and as their reactants, except that monoisocyanates should not be used as reactants for the urethane-containing compounds because they would lower the isocyanate functionality of the products obtained from the process according to the invention. The functionality of the products of this process can be varied both by suitable choice of the proportions in which the isocyanate components are mixed and by suitable choice of the proportions in which the various hydroxyl compounds are mixed.

The use of acids in the reaction of the urethane-containing compounds with the isocyanate components to produce the corresponding isocyanate-containing allophanate is essential to the invention. These acids are strong acids which split off protons and which react with aliphatic or cycloaliphatic isocyanates to form a mixed acid anhydride composed of the carbamic acid which corresponds to the isocyanate and the acid which splits off the protons. Suitable acids HX (X=acid group after removal of the proton) for the process according to the invention react with isocyanates Y—NCO to form adducts of the formula Y—NH—CO—X which are to be regarded as mixed anhydrides of the carbamic acid Y—NH—COOH and the acid HX. Examples of suitable acids include hydrohalic acids such as hydrogen fluoride, hydrogen chloride, hydrogen bromide and hydrogen iodide, chlorosulphonic acid, fluorosulphonic acid, sulphuric acid, alkane sulphonic acids such as methane sulphonic acid and perhalogenated alkane sulphonic acids such as trifluoro methane sulphonic acid. Hydrogen chloride is the preferred acid used for the process according to the invention.

The acids are used in quantities of from about 0.001 to 10.0%, preferably from about 0.01 to 1.0%, by weight in the process according to the invention, based on the total weight of the reactants.

They may be incorporated with the reaction mixture by any known method. For example, the acid may be added to the hydroxyl compound before the preparation of the compound which contains urethane groups. This is a convenient method of carrying out the process, especially when hydrogen chloride is used, because this compound is readily soluble in many hydroxyl compounds so that one can dispense with the introduction of small quantities of gaseous hydrogen chloride. Alternatively, the acid may be added together with the isocyanate components, either at the stage of the formation of the urethane-containing compounds or, if a two stage process is employed, at the stage of the preparation of the compounds which contain allophanate groups from the previously prepared compound containing urethane groups and a polyisocyanate component. Carbamic acid chloride derived either from the isocyanate used in the process or from some other isocyanate may, of course, also be used as catalyst. The use of an additional catalyst may be dispensed with if the diisocyanate is used in the form of a crude distillate which still contains a residue of more than about 0.001% by weight of hydrolizable chlorine, preferably in the form of carbamic acid chloride.

When carrying out the process according to the invention, the reactants are generally used in such quantities that from about 2 to 50, preferably from about 3 to 12, isocyanate groups of the polyisocyanate component, preferably a diisocyanate, are available for each urethane group of the compound which contains urethane groups. If the compound containing urethane groups is to be prepared in situ, the appropriate excess of isocyanate component, preferably diisocyanate component, is used.

The reaction according to the invention is generally carried out at a temperature within the range of from about 90° to 140° C. The progress of the reaction according to the invention can be followed by determining the isocyanate content of the reaction mixture. The reaction may be stopped at any time, for example by cooling the reaction mixture to room temperature or by removing the catalytically active acid, for example by applying a vacuum. This last mentioned method is suitable in particular when gaseous acids are used. Inactivation of the acid catalyst by the addition of compounds which react with the acids to form adducts, for example propylene oxide or an active unsaturated compound such as styrene, is another possible method of stopping the reaction.

The preferred variation of the process according to the invention, in which the starting compound which contains urethane groups is prepared in situ, is generally carried out as follows:

The diisocyanate which is preferably used as isocyanate component is introduced into the reaction vessel between about 50° to 80° C. and the hydroxyl component is added dropwise in the liquid form with vigorous stirring. If the same isocyanate or isocyanate mixture is to be used for urethane formation and allophanate formation, it is simplest to add it in such excess right from the beginning that the NCO/OH ratio is being approximately 3:1 and 12:1.

When the urethane reaction has taken place, which can be checked by determining the isocyanate content, the catalyst, generally hydrogen chloride is added. The temperature is then raised between about 90° and 140° C. and the reaction mixture is stirred until the isocyanate content has fallen to the value calculated for complete allophanatization.

At temperatures above about 130° C., it is advisable to keep the apparatus under a slight excess of pressure to prevent the escape of hydrogen chloride. If preferred, the catalyst may be introduced into the reaction vessel together with the isocyanate or it may be added together with the hydroxyl compound.

When the reaction has terminated, the catalyst can easily be removed by distillation under vacuum or by the addition of equivalent quantities of propylene oxide or an active unsaturated compound, to which it can be bound by chemical addition. If the polyisocyanate which contains allophanate groups is required to be freed for excess diisocyanate, this can be carried out either by thin layer distillation or by fractional extraction, for example using n-hexane or cyclohexane as extractant. In the first case, the hydrogen chloride may be left in the crude product because it is then distilled off together with the diisocyanate and finally contained in the distillate which can then be used for a fresh batch.

When carrying out the process according to the invention, the nature and quantitative proportions of the starting materials are generally chosen so that allophanates containing at least two isocyanate groups, i.e. allophanate polyisocyanates are obtained as products of the process. These products according to the invention are distinguished by their excellent stability during thin layer treatment even at temperatures of above 180° C. or more. The side reactions and equilibration reactions which are observed in the case of polyisocyanates with a biuret structure and which cause the formation of troublesome encrustations and an increase in viscosity do not occur.

The process according to the invention may suitably be carried out continuously. In that case, several reactors may be arranged one behind the other in the form of cascade. Diisocyanate, hydroxyl compound and catalyst are fed continuously into the first reactor. The temperature and rate of input are adjusted so that the reaction is completed by the time the reaction mixture leaves the last reactor. The crude product is then passed through a thin layer evaporator where it is freed from excess diisocyanate, which is then returned to the first reactor.

The allophanate polyisocyanates prepared according to the invention may be used for the production of polyurethane foams, elastomers, duromers, coatings and adhesives after removal of excess diisocyanate.

They are particularly suitable raw materials for the production of high quality lightfast and weather resistant lacquers, and may be used in combination with hydroxyl functional higher molecular weight compounds. In this field, the allophanate polyisocyanates are distinguished from polyisocyanates which have a urethane, biuret or isocyanurate structure by their good compatibility with commercial polyacrylates.

Another advantage of the process according to the invention lies in the wide range of possible variations, particularly with regard to the nature and proportions of inexpensive starting materials (hydroxyl-containing compounds). For example, the isocyanate functionality of the products obtained by the process according to the invention can be controlled within wide limits by suitable choice of the hydroxyl compound. The use of fatty alcohols gives rise to products which are readily soluble in petroleum hydrocarbons. Very hard lacquers are obtained by using cycloaliphatic or aromatic hydroxyl compounds.

The excellent storage stability of the allophanate polyisocyanates according to the invention when they have been freed from excess isocyanate used as a starting material should also be particularly mentioned. The products according to the invention show no tendency to split off monomeric isocyanate used as starting material and in this respect they differ particularly advantageously from the known biuret polyisocyanates.

The invention will be described in more detail with the aid of the following Examples.

EXAMPLE 1

150 g (1 mol) of triethylene glycol were added dropwise over a period of 30 minutes at 70° C. to 2016 g (12 mol) of hexamethylene diisocyanate in a 3 liter three-necked flask. After an additional 30 minutes at 70° C., the isocyanate content of the reaction mixture was 42.65%, which corresponded to complete conversion of the hydroxyl groups to urethane groups. 7 g of hydrogen chloride were then introduced and the temperature was raised to 100° C. After 8.5 hours, the isocyanate content of the reaction mixture was 38.8%, corresponding to complete conversion of the urethane groups to allophanate groups. The crude product was purified by thin layer distillation. 900 g of a yellowish product having a viscosity of 1200 cP/25° C. and an isocyanate content of 19.3% were obtained. The composition of the preparation was analyzed by gel chromatography (Table 1).

Comparison examples corresponding to British Pat. No. 994,890

A. (Without catalyst, as in Example 1 of the British Patent).

A solution of the bis-urethane in excess hexamethylene diisocyanate was first prepared as in the previous Example 1. A further fall in the isocyanate content to the value of 38.8% calculated for complete allophanatization could be obtained only after 48 hours at 135° to 145° C. The mixture was severely discolored by the end of this time. The product was worked up and analyzed as in Example 1 (Table 1). Viscosity: 1330 cP/25° C.; isocyanate content; 19.5%.

B. (Zinc naphthenate as catalyst as in Example 5 of the British Patent).

The urethane solution was prepared as in Example 1 above, and 2.3 g of zinc naphthenate were then added. The isocyanate content fell to 38.8% over a period of 8 hours at 50° C.

After working up (analysis Table 1):

Viscosity: 1350 cP/25° C.: isocyanate content: 20.4%

Color: brownish yellow

C. (Tertiary amine as catalyst as in Example 4 of the British Patent).

After the addition of 2.3 g of diazabicyclooctane to the urethane solution, the mixture was heated to 70° C. for 24 hours. The theoretical fall in isocyanate content was reached only after a further 16 hours at 120° C. When the reaction mixture was worked up, a deep yellow oil having a viscosity of 1050 cP/25° C. and an isocyanate content of 20.2% was obtained (analysis Table 1).

TABLE I
GEL CHROMATOGRAPHIC ANALYSIS

| Component (% by weight) | Example 1 | Comparison Examples | | |
|---|---|---|---|---|
| | | A | B | C |
| Hexamethylene diisocyanate | 0.5 | 0.6 | 0.7 | 0.5 |
| Dimeric diisocyanate | 1.5 | 5.8 | 1.5 | 6.3 |
| Trimeric diisocyanate | 1.0 | 7.3 | 10.6 | 11.3 |
| Bis-urethane from 1 mol of triethylene glycol and 2 mol of diisocyanate | — | 6.8 | 10.3 | 10.3 |
| Monourethane-monoallophanate from 1 mol of triethylene-glycol and 3 mol of diisocyanate | 7.0 | 18.3 | 9.8 | 15.6 |
| Bis-allophanate from 1 mol of triethylene glycol and 4 mol of diisocyanate | 44.7 | 16.5 | 20.8 | 12.2 |
| Sum of all the polymer-homologous compounds | 45.3 | 44.7 | 46.3 | 43.8 |

Comparison examples analogous to German Auslegeschrift Nos. 2,009,179 and 2,040,645 which describe the preparation of aromatic allophanate polyisocyanates.

D. A urethane solution (isocyanate content 36.85%) was first prepared from 1008 (6 mol) of hexamethylene diisocyanate and 106 g (1 mol) of diethylene glycol at 70° C. After the addition of 0.7 g of p-toluene-sulphonic acid methyl ester, the temperature was raised to 160° C. while anhydrous nitrogen was passed over the reaction mixture. The isocyanate content had fallen to 33.5% (calculated for complete allophanatization: 30.1%) after 50 hours. Since the reaction mixture was badly discolored by that time, the reaction was stopped at this point. IR spectroscopic analysis clearly indicated the presence of uretdione and isocyanurate groups.

E. A urethane solution (isocyanate content 41.4%) was prepared from 1008 g (6 mol) of hexamethylene diisocyanate and 57 g (0.75 mol) of 1,2-propylene glycol at 70° C. After the addition of 1 g of p-toluene-sulphonic acid methyl ester and 0.2 g of zinc acetylacetonate, the temperature was gradually raised to 110°-120° C. The isocyanate content of the reaction mixture fell to 38.1% over a period of 36 hours (calculated for complete allophanatization: 35.45%). The reaction mixture was discolored to a yellowish brown. The IR spectrum showed a strong isocyanurate band. When attempts were made to complete the reduction in isocyanate content at 150° to 160° C., an exothermic reaction suddenly set in with evolution of gas and the reaction mixture gelled completely.

EXAMPLE 2

120 g (0.5 mol) of molten 2,2-bis-(4-hydroxycyclohexyl)propane were added to 1512 g (9 mol) of hexamethylene diisocyanate at 100° C. A solution of 4 g of hydrogen chloride in 16 g (0.5 mol) of methanol was then added, also at 100° C. After an additional 9 hours at 100° C. under nitrogen, the isocyanate content was 38.27% (calculated for complete allophanate formation: 38.4%). The reaction mixture was then stirred up with 8 g of propylene oxide at 50° C. for 15 minutes. No more hydrolyzable chlorine could be detected at the end of this time. After degasification under vacuum, the crude product was subjected to thin layer distillation at 170° C./0.5 mm. 630 g of a colorless oil having a viscosity of 11,600 cP/25° C. and an isocyanate content of 17.4% were obtained. The residual hexamethylene diisocyanate content was 0.48%.

EXAMPLE 3

4 g of hydrogen chloride were introduced into 3024 g (18 mol) of hexamethylene diisocyanate at 90° C. 180 g (2 mol) of butane-1,4-diol were then added dropwise. After a further 1 hour, the temperature was raised to 100° C. After 8 hours under nitrogen, the isocyanate content of the mixture had fallen to 36.8%, which was the value calculated for complete allophanate formation. The mixture was stirred up with 10 g of propylene oxide at 50° C. and the product was then degasified under vacuum and distilled in a thin layer evaporator. 1415 g of a pale yellow liquid were obtained (distillate: 1750 g of hexamethylene diisocyanate).

Viscosity: 6,500 cP/25° C.;
Isocyanate content: 18.6%;
Residual diisocyanate content: 0.65%.
The IR spectrum showed traces of uretdione groups but no isocyanurate groups. A sample of the product was stored at 50° C. for 50 days. The residual hexamethylene diisocyanate content at the end of this time was found to be 0.66%.

EXAMPLE 4

1480 g of a highly viscous allophanate polyisocyanate with high functionality was prepared by a similar method to that of Example 1 from 3024 g (18 mol) of hexamethylene diisocyanate, 201 g (1.5 mol) of trimethylol propane and 8 g of hydrogen bromide as catalyst. When dissolved as an 80% solution in xylene/ethyl glycol acetate (1:1), the allophanate polyisocyanate had a viscosity of 2,800 cP/25° C. and an isocyanate content of 18.2%.

EXAMPLE 5

1008 g (6 mol) of hexamethylene disocyanate and 4 g of hydrogen chloride were added to 2150 g (1 mol) of a polyether of 80 mol % of ethylene oxide and 20 mol % of propylene oxide which had been started on n-butanol. The allophanate reaction was completed after 12 hours at 110° C. Thin layer treatment yielded 2,300 g of a pale yellow oil having a viscosity of 1200 cP/25° C. and an isocyanate content of 3.2%. The oil solidified to a waxy mass after some time.

EXAMPLE 6

A bi-functional allophanate having a viscosity of 200 cP/25° C. and an isocyanate content of 17.8% was prepared by a similar method to that of Example 1 from 3024 g (18 mol) of hexamethylene diisocyanate, 261 g (4.5 mol) of allyl alcohol and 7 g of hydrogen chloride as catalyst.

EXAMPLE 7

228 g (1 mol) of 2,2-bis-(4-hydroxyphenyl)-propane were melted and added dropwise from a heated dropping funnel to 2016 g (12 mol) of hexamethylene diisocyanate at 100° C. 5 g of hydrogen chloride were then introduced and the reaction mixture was stirred under nitrogen at 110° C. for 5 hours. The allophanate reaction was then completed (isocyanate content 37.5%). Thin layer distillation was carried out twice. 730 g of a viscous oil (viscosity 124,000 cP/25° C.) were then obtained. The oil solidified when left to stand for some time (softening point: 45° to 47° C.). The isocyanate content was 16.03%. The free hexamethylene diisocyanate content was 0.8% and did not increase when the reaction mixture was kept at 50° C. for 30 days (0.78%).

EXAMPLE 8

A mixture of 59 g (0.5 mol) of hexane-1,6-diol and 37 g of n-butanol was added to 1332 g (6 mol) of 3-isocyanatomethyl-3,5,5-trimethyl-cyclohexyl isocyanate-(1) at 100° C. 18 g of hydrogen chloride were introduced after 1 hour and the temperature was raised to 120° C. The allophanate reaction was completed after 18 hours (isocyanate content 27.6%). Thin layer distillation at 190° C. and 0.4 mm yielded a light colored resin which, when dissolved in ethyl glycol acetate to form an 80% solution, had a viscosity of 890 cP at 25° C. and an isocyanate content of 10.2%.

EXAMPLE 9

360 g of a highly viscous, colorless oil were obtained by the reaction of 630 g (3 mol) of 2,4,4-trimethyl-1,6-diisocyanate with 30 g (0.3 mol) of butane-1,4-diol and 1.5 g of hydrogen chloride for 6 hours at 110° C., followed by thin layer distillation. Viscosity: 150,000 cP/25° C.; isocyanate content: 15.3%.

EXAMPLE 10

A crude product was prepared from 678 g (3 mol) of 6-isocyanato-hexanoic acid-2-isocyanatoethyl ester, 39 g of hexane-1,6-diol (0.3 mol) and 1.5 g of hydrogen chloride, by heating to 110° C. for 5 hours. Thin layer distillation of this crude product yielded a light colored oil having a viscosity of 28,000 cP/25° C. (isocyanate content: 14.7%).

EXAMPLE 11

A solution of urethane in excess diisocyanate was prepared for 3024 g (18 mol) of hexamethylene diisocyanate and 152 g (2 mol) of propane-1,2-diol at 70° C. Various catalysts were added to separate portions of the mixture, each weighing 380 g, and the portions were left to react until the isocyanate content calculated for complete allophanatization was reached. The results are shown in the following table.

Table 2

| Catalyst | Quantity | Method of addition | Reaction time | Temperature |
|---|---|---|---|---|
| Sulphuric acid | 1.0 g | in 5 g of propylene glycol | 5 hours | 110° C. |
| Chlorosulphonic | 1.0 g | dissolved in 10 ml of methylene chloride | 4 hours | 110° C. |
| Methanesulphonic acid | 0.8 g | neat | 10 hours | 110° C. |

The products obtained showed no isocyanurate or uretdione band in the IR spectrum.

EXAMPLE 12 (Example of use)

154 g of 65% solution of a polyester of 6 mol of phthalic acid anhydride and 7 mol of trimethylolpropane (hydroxyl content 8%) in ethyl glycol acetate/Xylene (1:1) were diluted with 230 g of a solvent mixture of methylethylketone, butyl acetate, ethyl glycol acetate and toluene (4:1:4:1) after the addition of 1 g of a tertiary amine as catalyst and 0.4 g of cellulose-butyrate-propionate as levelling agent. 152 g of a 75% solution of the polyisocyanate from Example 2 in ethyl glycol acetate/Xylene (1:1) were added (NCO/OH molar ratio=1:1). The lacquer solution prepared in this way was applied to steel sheets to form lacquer films which hardened at room temperature. The completely hardened clear lacquer films were scratch resistant, elastic and resistant to solvents such as toluene, ethyl glycol acetate, ethyl acetate and acetone. They had the following properties:

| Thickness of layer | ca. 50 /µ |
|---|---|
| Erichsen cupping (DIN 53 156) | |
| after 6 days | 8.7 mm |
| after 9 days | 8.6 mm |
| Pendulum hardness (DIN 53 157) | |
| after 6 days | 238 seconds |
| after 8 days | 220 seconds |
| after 14 days | 227 seconds |

EXAMPLE 13 (Example of use)

154 g of the polyester solution described in Example 12 were made up into a paste with 100 g of titanium dioxide (rutile type). 140 g of the solvent mixture described above were added to this paste in addition to a catalyst and a levelling agent. 152 g of a 75% solution of the polyisocyanate from Example 1 in ethyl glycol acetate/Xylene (1:1) were added to the resulting mixture which was then applied in thin layers to steel sheets. The lacquer films containing pigment hardened completely through at room temperature. They were distinguished by their scratch resistance and solvent resistance and, compared with the clear lacquer films, they had the following properties:

| Thickness of layer | ca 50 /µ |
|---|---|
| Erichsen cupping (DIN 53 156) | |
| after 6 days | 8.1 mm |
| after 9 days | 8.0 mm |
| Pendulum hardness (DIN 53 157) | |
| after 6 days | 193 seconds |
| after 9 days | 187 seconds |
| after 14 days | 192 seconds |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for the preparation of allophanates containing aliphatically and/or cycloaliphatically bound isocyanate groups comprising reacting organic compounds which contain urethane groups with organic polyisocyanates containing aliphatically and/or cycloaliphatically bound isocyanate groups, characterized in that the reaction is carried out in the presence of strong acids which form a mixed carbamic acid anhydride with aliphatic or cycloaliphatic isocyanates.

2. The process according to claim 1, wherein the acids are used in a quantity of from about 0.001 to 10% by weight, based on the total weight of the reactants.

3. The process according to claim 1, wherein the acid used is a hydrogen halide.

4. The process of claim 1, wherein the organic compounds containing urethane groups are prepared in situ from phenols or alcohols and excess quantities of aliphatic or cycloaliphatic polyisocyanates.

5. A process for the preparation of isocyanate-containing allophanates comprising reacting compounds of the general formula $$A-(O-\overset{O}{\underset{\|}{C}}-NH-R_1-NCO)_n$$

wherein
A represents a group of the kind obtained by removal of the hydroxyl groups from an organic compound with a valency of n which contains hydroxyl groups and which, apart from its hydroxyl groups, is inert towards isocyanate groups:
$R_1$ represents a group of the kind obtained by removal of the isocyanate groups from a diisocyanate which has aliphatically and/or cycloaliphatically bound isocyanate groups, and
n represents an integer of from about 1 to 4,
with polyisocyanates of the general formula $$R_2(NCO)_n$$

wherein
$R_2$ represents an aliphatic hydrocarbon group with from about 2 to 20, carbon atoms, a cycloaliphatic hydrocarbon group with from about 4 to 20, carbon atoms or a xylylene group, and
n represents an integer of either 2 or 3,
characterized in that the reaction is carried out in the presence of strong acids which form a mixed carbamic acid anhydride with aliphatic or cycloaliphatic isocyanates.

6. The process of either claim 1 or 5 wherein from about 2 to 50 isocyanate groups of the polyisocyanate component are available for each urethane group.

7. The process of either claim 1 or 5, wherein the reaction is carried out at a temperature of from about 90° to 140° C.

8. The process of either claim 1 or 5, wherein the organic polyisocyanates are diisocyanates.

9. The product produced by the process of either claim 1 or 5.

10. A process for the production of storage stable allophanate polyisocyanates comprising reacting
(i) organic compounds which contain urethane groups with
(ii) organic polyisocyanates containing aliphatically and/or cycloaliphatically bound isocyanate groups,
characterized in that the reaction is carried out in the presence of strong acids which form a mixed carbamic acid anhydride with aliphatic or cycloaliphatic isocyanates and any excess isocyanate is removed from the reaction mixture.

11. A process for the production of lacquers comprising reacting the allophanate containing isocyanates produced by the process of either claim 1 or 5 with polyhydroxyl components.

12. Lacquers produced by the process of claim 11.

13. A process for coating comprising applying the lacquers produced by the process of claim 11 to a substrate.

* * * * *